United States Patent [19]

Orth

[11] Patent Number: 5,542,925

[45] Date of Patent: Aug. 6, 1996

[54] DILATATION CATHETER WITH OBLONG PERFUSION PORTS

[75] Inventor: Jean C. Orth, San Jose, Calif.

[73] Assignee: Advanced Cardiovascular Systems, Inc., Santa Clara, Calif.

[21] Appl. No.: 387,977

[22] Filed: Feb. 13, 1995

Related U.S. Application Data

[63] Continuation of Ser. No. 148,000, Nov. 5, 1993, abandoned.

[51] Int. Cl.$^6$ .................................................. A61M 29/00
[52] U.S. Cl. .......................................... 604/102; 606/192
[58] Field of Search ........................... 604/96–103, 264, 604/280; 606/192–196

[56] References Cited

U.S. PATENT DOCUMENTS

| | | | |
|---|---|---|---|
| 4,581,017 | 4/1986 | Sahota | 604/101 |
| 4,639,252 | 1/1987 | Kelly et al. | 604/282 |
| 4,771,777 | 9/1988 | Horzewski et al. | 604/102 X |
| 4,790,315 | 12/1988 | Mueller, Jr. et al. | 604/96 X |
| 4,892,519 | 1/1990 | Songer et al. | 604/96 |
| 5,037,403 | 8/1991 | Garcia | 604/280 |
| 5,046,503 | 9/1991 | Schneiderman | 128/692 |
| 5,087,247 | 2/1992 | Horn et al. | 604/98 |
| 5,135,474 | 8/1992 | Swan et al. | 604/8 |
| 5,201,723 | 4/1993 | Quinn | 604/204 |
| 5,295,961 | 3/1994 | Niederhauser et al. | 604/96 |
| 5,370,617 | 12/1994 | Sahota | 604/102 |

FOREIGN PATENT DOCUMENTS

| | | | |
|---|---|---|---|
| 0441384 | 8/1991 | European Pat. Off. | 604/102 |

*Primary Examiner*—John D. Yasko
*Assistant Examiner*—Adam J. Cermak
*Attorney, Agent, or Firm*—Crosby, Heafey, Roach & May

[57] ABSTRACT

A dilatation catheter is described wherein a plurality of oblong perfusion ports are provided in the catheter shaft to provide perfusion flow of blood through the distal section of the catheter. Oblong perfusion ports are preferably provided both proximal and distal to the inflatable dilatation balloon. Orienting the long dimensions of the oblong perfusion ports at an angle from the longitudinal axis of the catheter shaft minimizes kinking of the catheter shaft when passing through tortuous passageways.

13 Claims, 2 Drawing Sheets

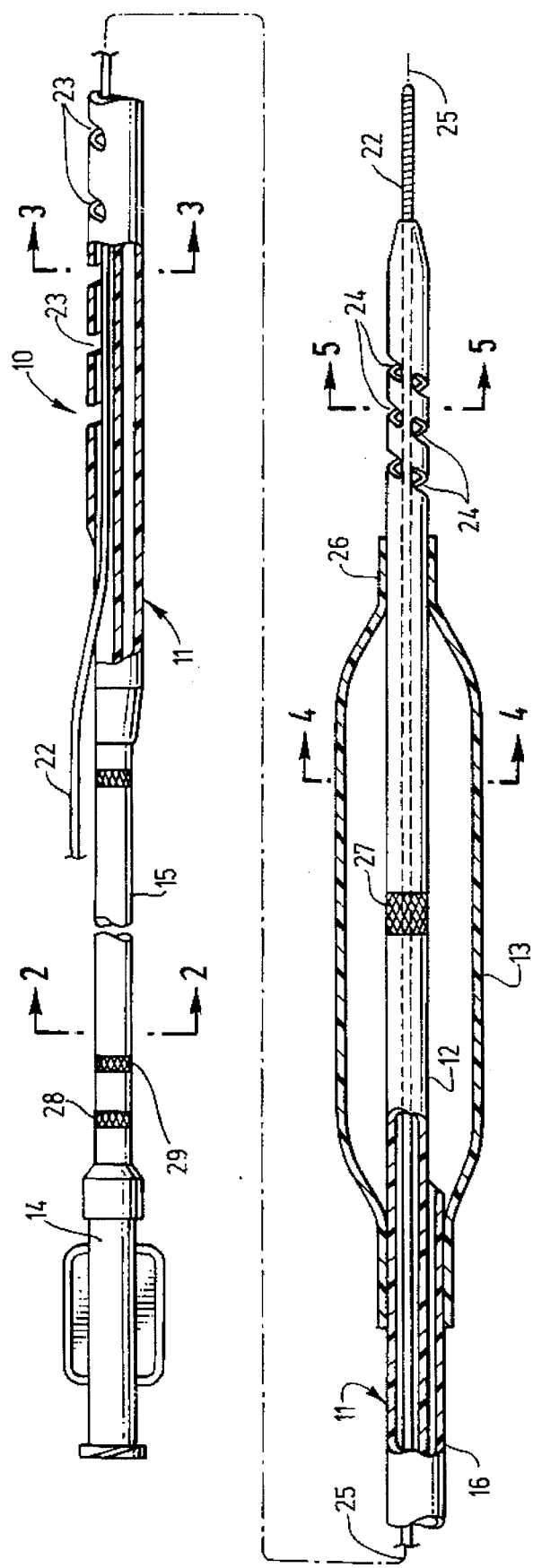
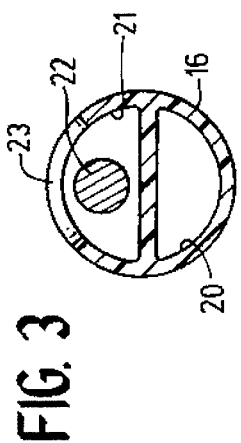
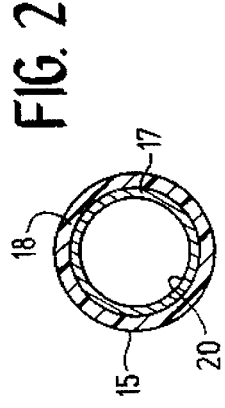
FIG. 1
FIG. 2
FIG. 3

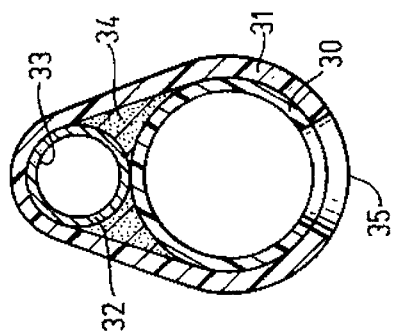
FIG. 5
FIG. 7
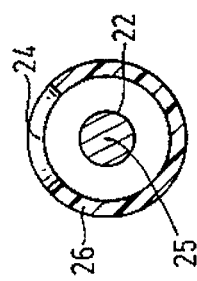
FIG. 4
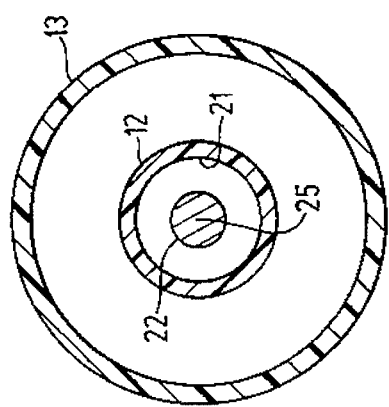
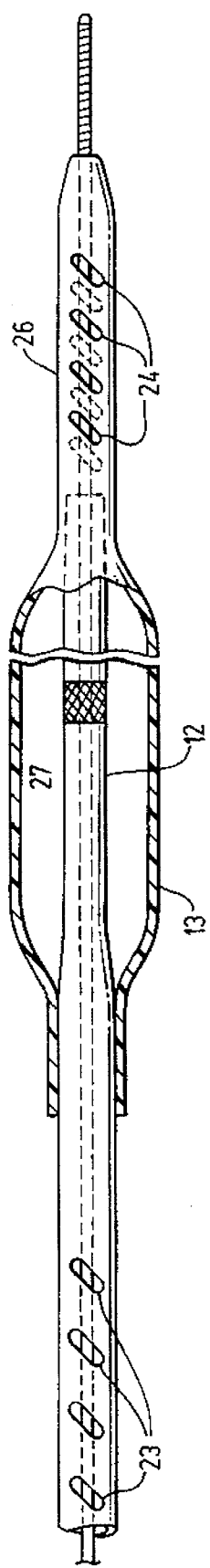
FIG. 6

DILATATION CATHETER WITH OBLONG PERFUSION PORTS

This is a continuation of application Ser. No. 08/148,000 which was filed on Nov. 5, 1993, (now abandoned).

BACKGROUND OF THE INVENTION

This invention generally relates to perfusion type intravascular catheters and particularly to perfusion type balloon dilatation catheters used in percutaneous transluminal coronary angioplasty (PTCA).

In typical PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from the proximal end to turn the distal tip of the guiding catheter so that it can be seated in the desired coronary ostium. With over-the-wire balloon dilatation catheter systems, a guidewire and a balloon dilatation catheter are introduced into and advanced through the guiding catheter to the distal tip thereof, with the guidewire slidably disposed within an inner lumen of the dilatation catheter. The guidewire is first advanced out the distal tip of the guiding catheter until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. One or more inflations may be necessary to effectively dilate the stenosis. Additional stenoses may be dilatated with the same catheter. When the dilatations have been completed, the balloon is deflated so that the dilatation catheter can be removed from the dilated stenosis and an adequated blood flow will resume through the dilated artery.

The assignee of the present application, Advanced Cardiovascular Systems, Inc., has introduced improved dilatation catheters into the market place under the trademarks STACK PERFUSION® Coronary Dilatation Catheter and the RX Perfusion™ Dilatation catheter which have a plurality of perfusion ports in the wall of the catheter shaft proximal to the balloon and has one or more perfusion ports in the catheter shaft distal to the balloon. The perfusion ports are in fluid communication with a guidewire receiving inner lumen which extends to a guidewire port in the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the inflated balloon to thereby prevent or minimize ischemic conditions in tissue distal to the catheter when the balloon is inflated. As is appreciated by those skilled in the art, tissue distal to a stenosis is frequently already in jeopardy due to ischemic conditions which may result from the stenotic region within the artery. Therefore, care must be exercised in sizing the perfusion ports and the inner lumen to ensure that there is adequate flow of oxygenated blood to tissue distal to the catheter during the dilatation to eliminate or minimize resulting ischemic conditions. These perfusion catheters have been widely praised and have met with much commercial success.

The ACS RX® Perfusion Coronary Dilatation Catheter is described and claimed in copending application Ser. No. 07/888,253, filed on May 22, 1992, which is incorporated herein in its entirety by reference. The catheter described in the aforesaid copending application has a short guidewire receiving sleeve or inner lumen extending through a distal portion of the catheter a short distance from a first guidewire port in the distal end of the catheter to a second guidewire port in the catheter spaced proximally a short distance from the inflatable member of the catheter. The second guidewire port is spaced a substantial distance from the proximal end of the catheter and usually about 10 to about 50 cm from the first guidewire port in the distal end of the catheter. A slit in communication with the guidewire receiving inner lumen may be provided in the wall of the catheter body which extends distally from the second guidewire port to a location proximal to the perfusion ports which are proximal to the inflatable balloon. The structure of this catheter allows for the rapid exchange of the catheter without the need for an exchange wire or adding a guidewire extension to the proximal end of the guidewire and the additional feature of providing perfusion of oxygenated blood distal to the catheter when the balloon is inflated within the patient's coronary artery.

One of the problems encountered with the use of perfusion type catheters has been that it is not uncommon for the guidewire to pass through a perfusion port when it is advanced through the inner lumen of the catheter. Efforts have been made to eliminate this problem by providing a barrier within the perfusion port(s) but this has not met with much success. For example, perfusion catheters have been designed wherein a single perfusion port is provided proximal to the inflatable balloon which is has an interior barrier to prevent the excursion of a guidewire through the single perfusion port. However, in this design, if for some reason the single port is pressed against the arterial wall or otherwise blocked or occluded, the flow of oxygenated blood distal to the catheter can be reduced considerably causing the patient to be put in jeopardy due to the ischemic conditions which may be created.

What has been needed and heretofore unavailable is a perfusion type intravascular catheter which will prevent guidewire excursions through the perfusion ports and will also ensure an adequate flow of oxygenated blood distal to the catheter to prevent dangerous ischemic conditions from existing distal to the catheter for any significant periods of time. The present invention satisfies these and other needs.

SUMMARY OF THE INVENTION

This invention is directed to a perfusion type intravascular catheter which precludes excursion of a guidewire through a perfusion port when the guidewire is advanced through the interior of the catheter.

The catheter of the invention generally includes an elongated catheter shaft with proximal and distal sections, a distal end with a guidewire port therein, means to perform an intravascular procedure on the distal section of the catheter shaft and a guidewire receiving inner lumen which extends at least within the distal section of the catheter shaft to the guidewire port in the distal end of the catheter shaft. The catheter is adapted to be advanced over a guidewire which is slidably disposed within the inner lumen. In accordance with the invention, oblong perfusion ports are provided in one or more wall portions of the distal section of the catheter shaft which defines at least part of the guidewire receiving inner lumen. The perfusion ports preferably have lengths which are at least 50% greater than their widths, and the widths of the perfusion ports are dimensioned to be small enough to prevent the passage of a guidewire therethrough. The widths of the oblong perfusion parts may range from about 0.003 to about 0.012 inch, preferably about 0.005 to about 0.01 inch. The length may vary from about 0.02 at least 0.015, preferably about 0.02 to about 0.04 inch. The overall area of all of the oblong perfusion ports and the transverse cross-sectional area of the guidewire receiving inner lumen are large enough to ensure the perfusion of an adequate volume of oxygenated blood through the inner lumen in the distal shaft section to a location distal to the catheter. To minimize kinking of the distal shaft section which has oblong perfusion ports, the long dimensions of the oblong ports are inclined at a angle, preferably from about 30° to about 60° with respect to a longitudinal axis which extends through the central portion of the catheter shaft.

A presently preferred embodiment of the invention is directed to a dilatation catheter for angioplasty procedures which has a inflatable member on the distal shaft section, such as a balloon, for dilating a stenotic region of a patient's coronary artery. The balloon is disposed about a distally extending tubular element of the catheter shaft with the distal end of the inflatable member sealingly secured about the distal end of the tubular element. The proximal end of the inflatable member is sealingly secured about a distal portion of the catheter shaft distal to the inflation port.

In one presently preferred embodiment, the distal portion of the catheter shaft proximal to the perfusion port is provided with a guidewire receiving port which is in fluid communication with the inner lumen within the catheter shaft, such as described in U.S. Pat. No. 5,040,548 (Yock), No. 5,061,273 (Yock) and No. 4,748,982 (Horzewski et al), which are incorporated herein. The guidewire port in the proximal section is spaced longitudinally from the guidewire port in the distal end of the tubular element a short distance, e.g. about 10 cm to about 35 cm, but generally is not spaced a distance greater than about 50 cm. In this embodiment, it is preferred that the proximal portion of the catheter shaft have a greater degree of stiffness to aid in pushing the catheter over a guidewire. The proximal shaft portion is preferably formed, at least in part, of hypotubing as described in U.S. Pat. No. 5,154,725 (Leopold).

The catheter of the invention provides for an increased perfusion flow of blood through the catheter and ensures that the guidewire does not pass through a perfusion port in the wall portion of the catheter shaft. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is an elevational view, partially in section, of the distal section of the catheter shown in FIG. 1 which has been rotated 90° about its longitudinal axis from its position shown in FIG. 1.

FIG. 7 is a transverse cross sectional view of an alternative catheter shaft construction in the distal portion thereof.

DETAILED DESCRIPTION OF THE INVENTION

A catheter 10 embodying features of the invention, which is depicted in FIGS. 1–6, generally includes a catheter shaft 11, a distal tubular extension 12, a balloon 13 disposed about the tubular extension, and an adapter 14 which is secured to the proximal end of the catheter shaft.

The catheter shaft 11 includes a proximal section 15 and a distal section 16. The proximal section 15 is formed of hypotubing 17 having a plastic outer coating or jacket 18, as shown in FIG. 2, and is generally stiffer than the distal section 16. The distal section 16 is of a dual lumen design, as best shown in FIG. 3, with a first inner lumen 20 which directs inflation fluid to the interior of the balloon 13 and second inner lumen 21 which slidably receives a guidewire 22. The distal end of the hypotube 17 is usually tapered and interfits into the first inner lumen 20 in the proximal end of the distal section 16.

As best shown in FIGS. 1 and 6, a plurality of proximal oblong perfusion ports 23 are provided in the distal section 16 of the catheter shaft 11 proximal to the balloon 13 and a plurality of distal oblong perfusion ports 24 distal to the balloon. As shown, both sets of perfusion ports 23 and 24 are inclined along their long dimension at an angle from the longitudinal axis 25 of the catheter shaft 11 and both are in fluid communication with the guidewire receiving inner lumen 21.

The distal tubular extension 12 which extends through the interior of the balloon is formed as part of the catheter shaft and the distal end thereof is secured to the distal skirt 26 of the inflatable balloon 13 as shown in FIGS. 1 and 6.

Radiopaque marker 27 is provided on the tubular extension 12 at the midpoint of the balloon 13 to facilitate fluoroscopic location of the balloon within the patient. Visual markers 28 and 29 are provided on the proximal section of the catheter shaft 11, with marker 28 being the femoral marker located about 105 cm from the distal end of the catheter and marker 29 being the brachial marker located about 95 cm from the distal end of the catheter.

FIG. 7 illustrates an alternative embodiment of the invention wherein the distal section 16 of the catheter shaft 11 has an inner tubular member 30 and an outer tubular member 31, with a significant portion of the outer tubular member being secured to the exterior of the inner tubular member, as shown. This figure is a transverse cross-sectional view of a distal portion of the catheter shaft proximal to an inflatable member as in FIG. 3. Preferably, the outer tubular member 31 is formed of a heat shrinkable plastic material which is heat shrunk onto the exterior of the inner tubular member 30, and which has a tubular support member 32 between the inner and outer tubular members and to form the inflation lumen 33. The outer tubular member 31 may also be fusion bonded or adhesively bonded to the inner tubular member 30. Filler material 34, e.g. polyethylene, may be provided between the tubular support member 32 and the inner and outer tubular members 30 and 31 to fill in any gaps which might form. Oblong perfusion port 35, as previously described, is provided in the bonded section between the inner tubular member 30 and the outer tubular member 31. The rest of the catheter is essentially the same as that shown in FIGS. 1–6. This catheter construction is disclosed in co-pending application Ser. No. 07/870,820, filed on Apr. 20, 1992, entitled LOW PROFILE DILATATION CATHETER, which is incorporated herein by reference in its entirety.

The materials of construction can be of a conventional nature. The hypotube 17 can be formed of stainless steel or a superelastic NiTi alloy, such as described and claimed in copending application Ser. No. 07/629,381, filed Dec. 18, 1990, and incorporated herein by reference, and the coating or jacket 18 thereon can be a polyethylene tubing heat shrunk onto the exterior of the hypotube. The catheter shaft forming the distal section 16, the tubular extension 12 and the inner and outer tubular members 30 and 31 may be formed of mixture of high and low density heat shrinkable polyethylene. Generally the inner member is predominately high density polyethylene and the outer tubular member is predominantly low density polyethylene. The balloon 13 may be formed of polyethylene, polyethylene terephthalate, olefinic ionomers such as Suryln® (sold by E. I. dupont, deNemours & Co.) and other suitable materials. The balloon may be a formed-in-place balloon which is described in copending application Ser. No. 07/758,630, filed Sep. 12, 1991, entitled FORMED IN PLACE BALLOON FOR VASCULAR CATHETER and which is incorporated herein by reference. The support member may be formed of polyamide. The joints between the various members of the catheter can be made by heat bonding or by means of a suitable adhesive such a cyanoacrylate adhesive sold under the trademark Loctite™, e.g. 405 and 415. The dimensions of the catheter are for the most part conventional. The overall length of the catheter, excluding the adapter is about 135 cm, the length of the distal section is about 25–30 cm and the length of the cylindrical working surface of the balloon is about 2 cm. The maximum inflated diameters of the balloon generally range from about 1 to about 4 mm. The transverse dimensions of the catheter shaft are to a large measure controlled by the outer diameter of the guidewire to be used in the angioplasty procedure. The guidewires conventionally used for coronary artery use have outer diameters ranging from about 0.008 to about 0.022 inch (0.25 to 0.46 mm). The inner diameters of the guidewire receiving inner lumens for guidewires of this size generally range from about 0.012 to about 0.024 inch (0.38 to 0.56 mm). Typical wall thicknesses for the inner and outer tubular members is about 0.002 inch (0.051 mm). The wall thickness of the balloon varies depending upon the material from which it is made and the level of pressure the balloon is to experience upon inflation during the angioplasty procedure. The cross-sectional area of the perfusion port can vary depending upon the size of the catheter and the size of the artery into which the catheter is to be deployed.

The invention has been described herein primarily with respect to dilatation catheters having rapid exchange features, namely, a short guidewire receiving inner lumen within the distal section of the catheter with a proximal guidewire port spaced proximately from a distal guidewire port in the distal end of the catheter. However, the features of the invention can be employed in a wide variety of perfusion type catheters used in various body lumens.

What is claimed is:

1. A perfusion type intravascular catheter assembly including a catheter with an inner lumen extending therein and a guidewire having a predetermined diameter slidably disposed within the lumen of the catheter, comprising:

a) an elongated catheter shaft having proximal and distal ends, a guidewire port in the distal end with the inner lumen which slidably receives the guidewire having a predetermined diameter and which extends at least within a distal section of the catheter shaft and is in fluid communication with the guidewire port in the distal end of the catheter shaft;

b) expandable means on the distal section of the catheter shaft spaced from the distal end of the shaft which occludes the patient's artery when expanded; and c) a plurality of oblong perfusion ports having a major and a minor axis in a wall portion of the distal shaft section proximal to the expanding means which are in fluid communication with the guidewire receiving inner lumen and wherein the minor axis is smaller than the predetermined diameter of the guidewire and the major axis is greater than the predetermined diameter of the guidewire.

2. The catheter assembly of claim 1 wherein the expandable means is a dilatation balloon having an interior adapted to receive inflation fluid.

3. The catheter assembly of claim 2 wherein the catheter shaft has an inflation lumen which extends therein and which is in fluid communication with the interior of the dilatation balloon.

4. The catheter assembly of claim 3 wherein the catheter shaft has means on the proximal end thereof to inject inflation fluid through the inflation lumen to the interior of the dilatation balloon.

5. The catheter assembly of claim 1 wherein the distal shaft section has at least one oblong perfusion port in the wall thereof distal to the expandable member.

6. The catheter assembly of claim 1 including a guidewire port in the proximal section of the catheter shaft in fluid communication with the guidewire receiving lumen and spaced proximally a short distance from the perfusion ports.

7. The catheter assembly of claim 1 wherein the distal section of the catheter shaft has inner and outer tubular members, with the outer tubular member being secured to the exterior of the inner tubular member for a significant portion thereof and having an unsecured portion which defines the inflation lumen.

8. The catheter assembly of claim 1 wherein the oblong perfusion ports have a width which is less than half the length thereof.

9. The catheter assembly of claim 1 wherein the oblong perfusion ports have a width less than the preselected diameter of the guidewire which the inner lumen of the catheter shaft is configured to slidably received therein.

10. The catheter assembly of claim 9 wherein the oblong perfusion ports have maximum widths of about 0.002 to about 0.012 inch.

11. The catheter assembly of claim 10 wherein the oblong perfusion ports have lengths of at least about 0.015 inch.

12. The catheter assembly of claim 10 wherein the oblong perfusion ports have lengths of about 0.02 to about 0.04 inch.

13. The catheter assembly of claim 9 wherein the oblong perfusion ports have maximum widths of about 0.004 to about 0.010 inch.

* * * * *